United States Patent
Ozaki et al.

(10) Patent No.: US 9,585,542 B2
(45) Date of Patent: Mar. 7, 2017

(54) IMAGING SYSTEM AND IMAGING DEVICE

(71) Applicant: OLYMPUS CORPORATION, Hachioji-shi, Tokyo (JP)

(72) Inventors: Takashi Ozaki, Tokyo (JP); Yugo Koizumi, Yokohama (JP); Daisuke Sano, Yokohama (JP); Ken Suzuki, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/143,714

(22) Filed: May 2, 2016

(65) Prior Publication Data

US 2016/0242628 A1  Aug. 25, 2016

Related U.S. Application Data

(63) Continuation of application No. PCT/JP2014/082243, filed on Dec. 5, 2014.

(30) Foreign Application Priority Data

Dec. 19, 2013  (JP) ................. 2013-262012

(51) Int. Cl.
*A61B 1/00* (2006.01)
*G06F 19/00* (2011.01)
*A61B 1/04* (2006.01)

(52) U.S. Cl.
CPC ...... *A61B 1/00011* (2013.01); *A61B 1/00006* (2013.01); *A61B 1/00032* (2013.01);
(Continued)

(58) Field of Classification Search
CPC .......... H04L 41/0896; H04N 21/23614; H04N 21/2402; H04N 1/00127; H04N 1/33353;
(Continued)

(56) References Cited

U.S. PATENT DOCUMENTS 6,014,694 A * 1/2000 Aharoni ........... H04N 21/23438
370/232
7,050,184 B1 * 5/2006 Miyamoto ......... H04N 1/00127
358/1.13

(Continued)

FOREIGN PATENT DOCUMENTS

JP      111-27316 A     1/1999
JP    2002-034907 A     2/2002

(Continued)

OTHER PUBLICATIONS

Mar. 17, 2015 International Search Report issued in International Patent Application No. PCT/JP2014/082243.

(Continued)

*Primary Examiner* — Nathnael Aynalem
(74) *Attorney, Agent, or Firm* — Oliff PLC

(57) ABSTRACT

An imaging system includes an imaging device connected to a first communication network, and a first server device connected to the first communication network, and each of the imaging device and the first server device includes a first logical port that is used to transfer video data, a second logical port that is used to transfer data other than the video data, a measuring unit that measures a data transfer amount of the second logical port, and a band control unit that controls transfer bands of the first logical port and the second logical port according to the data transfer amount measured by the measuring unit.

13 Claims, 10 Drawing Sheets

(52) U.S. Cl.
CPC .............. *A61B 1/04* (2013.01); *G06F 19/321* (2013.01); *A61B 1/00009* (2013.01)

(58) Field of Classification Search
CPC ........ H04N 2201/0039; A61B 1/00006; A61B 1/00009; A61B 1/00011; A61B 1/00032; A61B 1/04; G06F 19/321
USPC ..................................................... 348/45, 65
See application file for complete search history.

(56) References Cited

U.S. PATENT DOCUMENTS

| | | | | |
|---|---|---|---|---|
| 8,780,978 | B2* | 7/2014 | Polisetty | ................. G10L 25/78 375/240.03 |
| 2002/0018587 | A1 | 2/2002 | Ueda | |
| 2010/0273142 | A1 | 10/2010 | Prins et al. | |
| 2013/0067524 | A1* | 3/2013 | Andrews | .......... H04N 21/23436 725/109 |
| 2013/0300829 | A1 | 11/2013 | Urasaki et al. | |

FOREIGN PATENT DOCUMENTS

| | | |
|---|---|---|
| JP | 2002-058017 A | 2/2002 |
| JP | 2008-284037 A | 11/2008 |
| JP | 2010-046216 A | 3/2010 |
| JP | 2011-024946 A | 2/2011 |
| JP | 2011-508203 A | 3/2011 |
| JP | 5331948 B2 | 10/2013 |
| WO | 2009/083862 A1 | 7/2009 |
| WO | 2013/031512 A1 | 3/2013 |

OTHER PUBLICATIONS

Mar. 17, 2015 Written Opinion issued in International Patent Application No. PCT/JP2014/082243.
Jan. 19, 2016 Decision to Grant issued in Japanese Patent Application No. 2015-530208.
Sep. 24, 2015 Office Action issued in Japanese Patent Application No. 2015-530208.

* cited by examiner

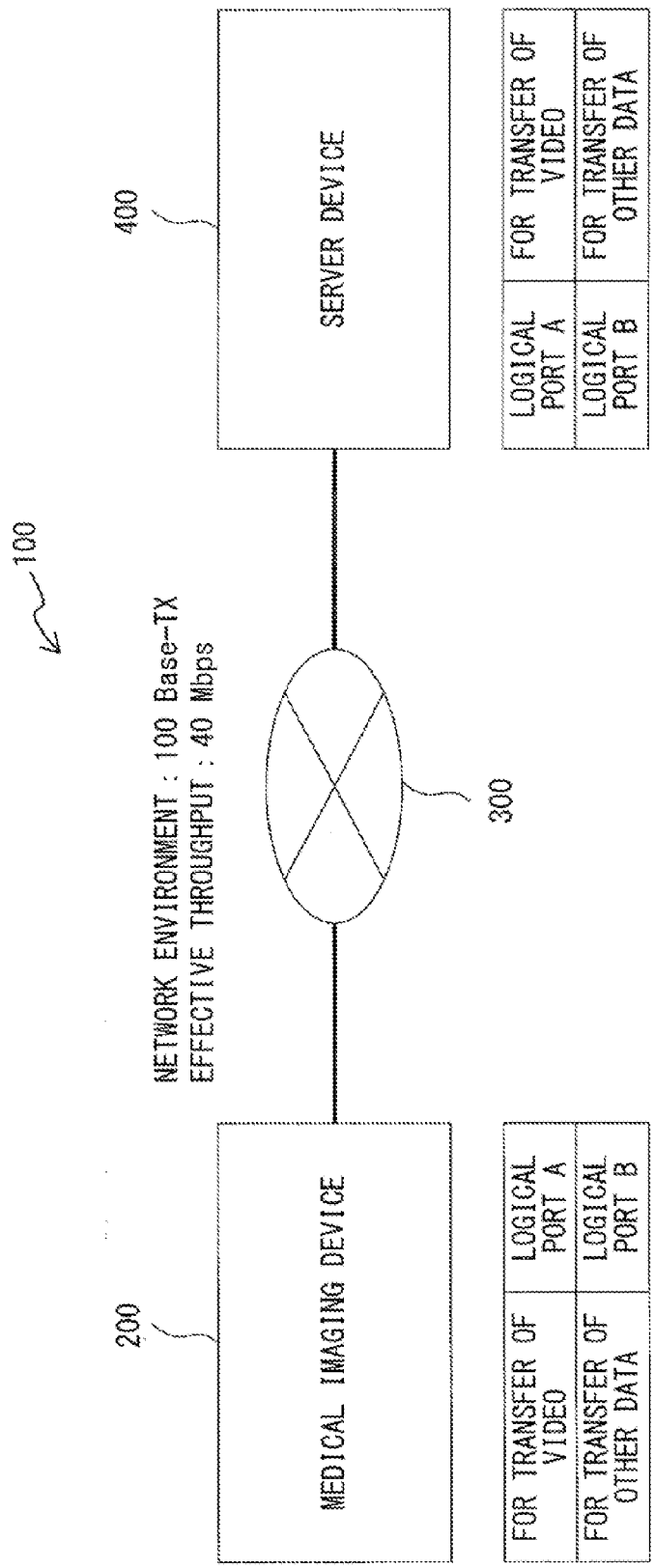
F I G. 1

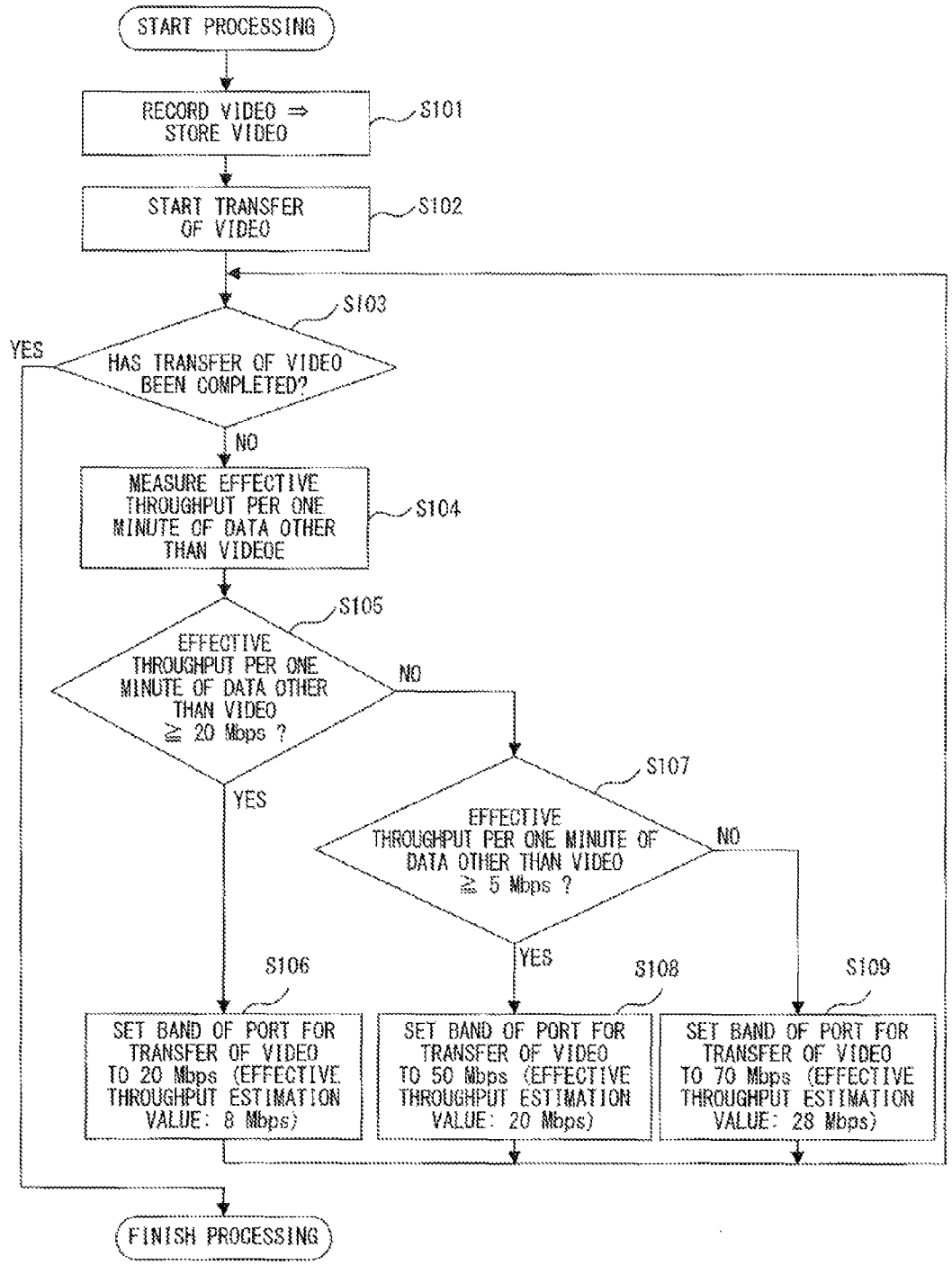
F I G. 3

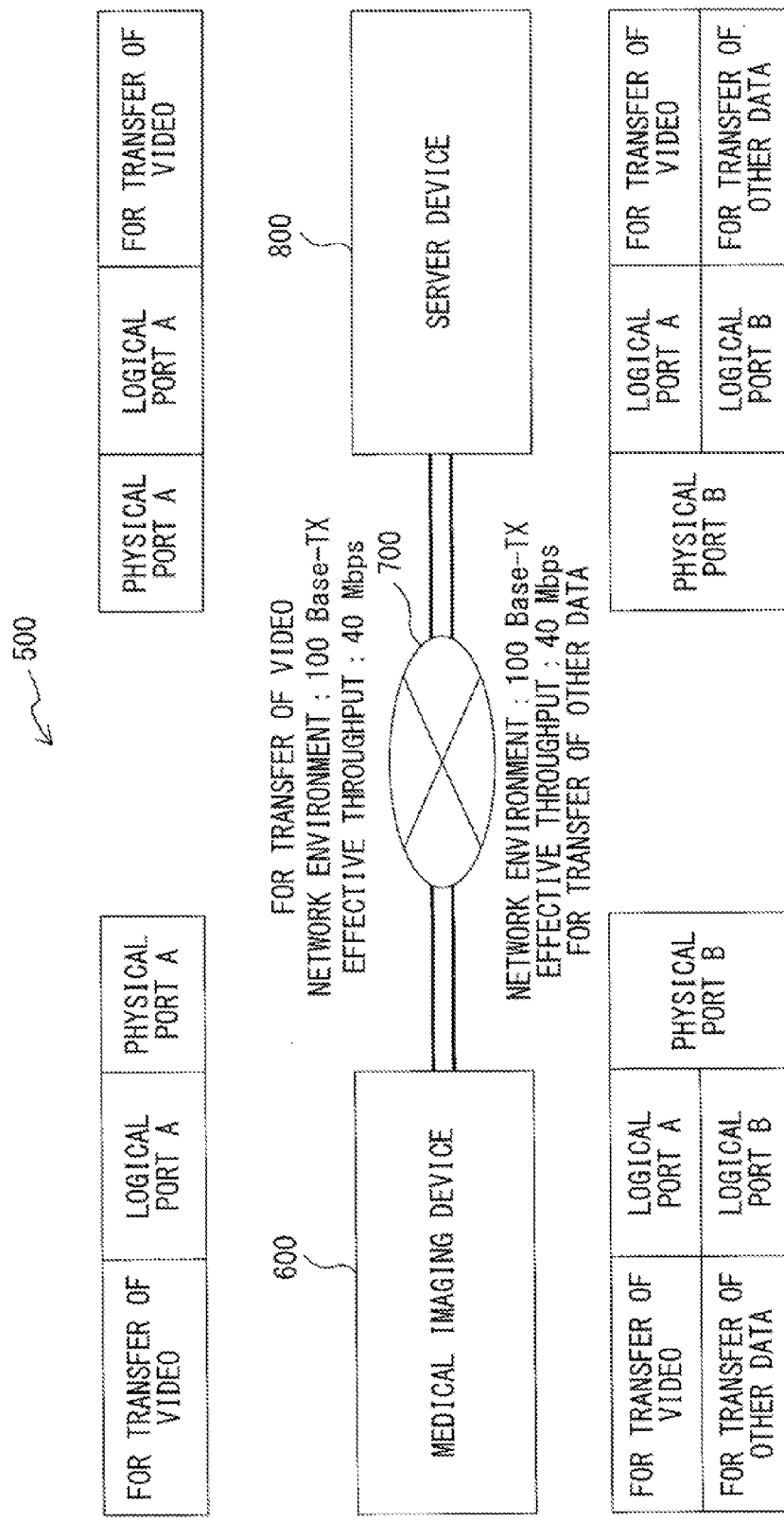
F I G. 4

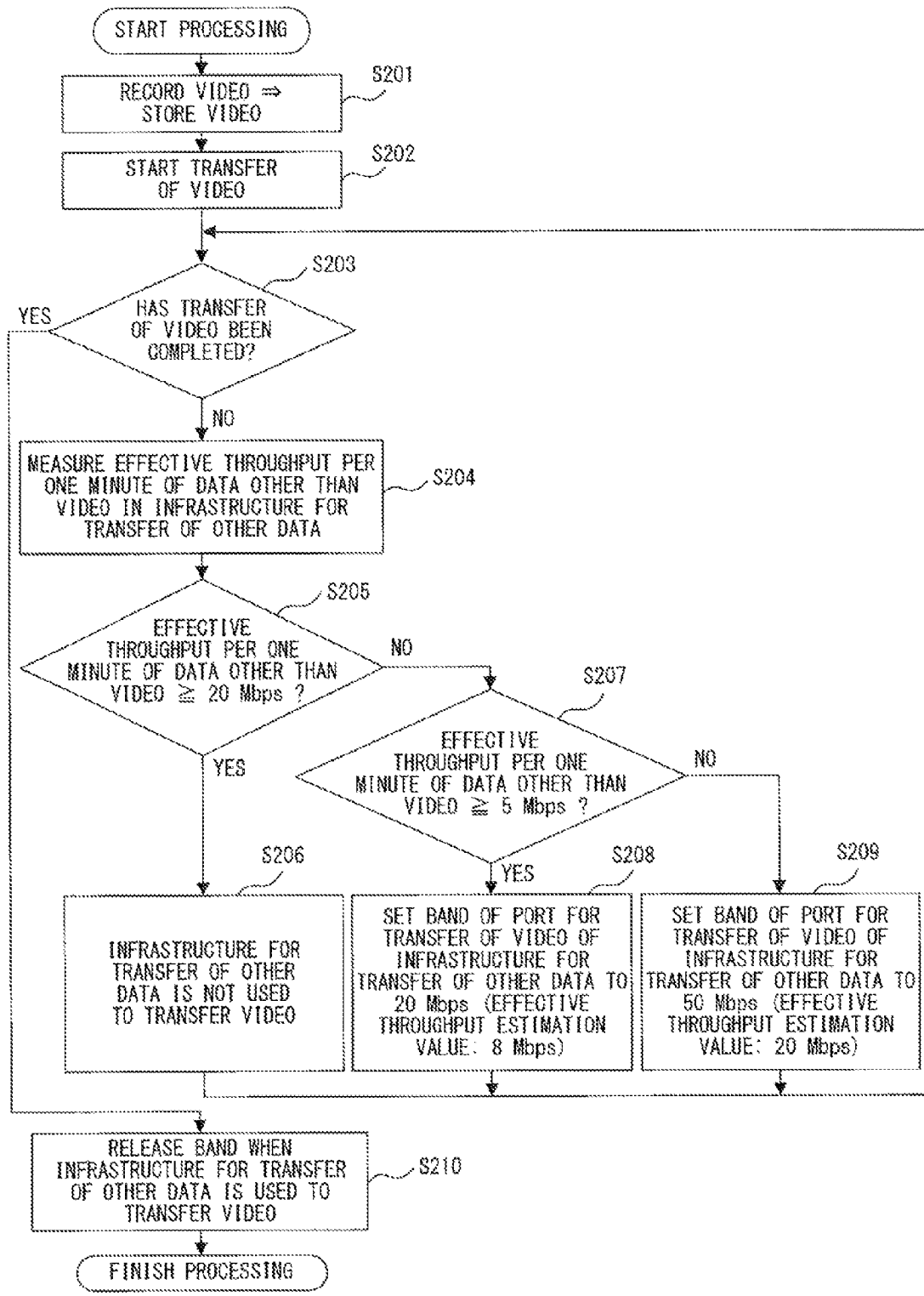
F I G. 6

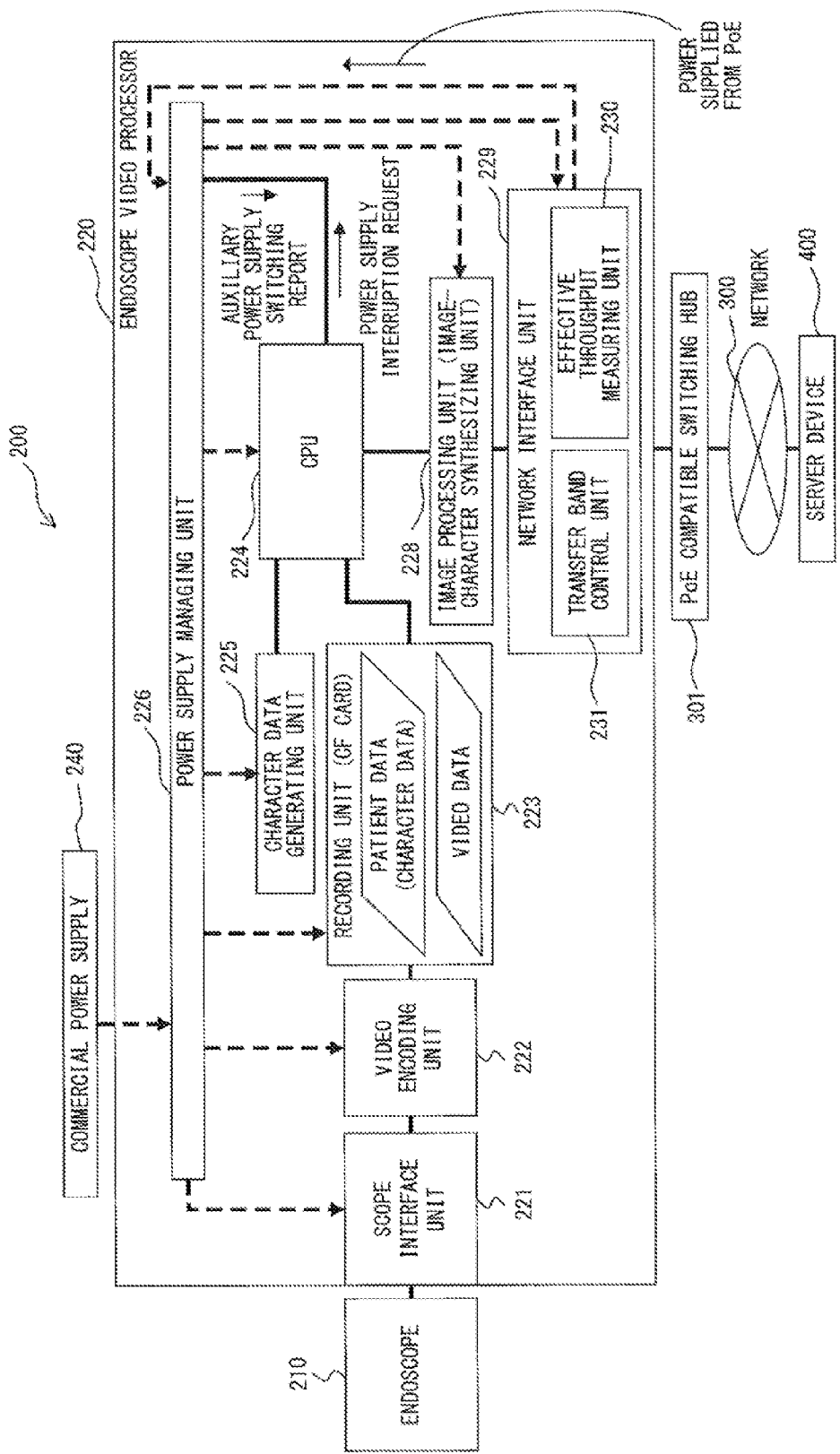
F I G. 7

IMAGING SYSTEM AND IMAGING DEVICE

CROSS-REFERENCE TO RELATED APPLICATIONS

This application is based upon and claims the benefit of priority of the prior Japanese Patent Application No. 2013-262012, filed Dec. 19, 2013, the entire contents of which are incorporated herein by reference.

This is a Continuation Application of PCT Application. No. PCT/JP2014/082243, filed Dec. 5, 2014, which was not published under PCT Article 21(2) in English.

FIELD

The present invention relates to an imaging system including an imaging device and a server device.

BACKGROUND

Conventionally, an imaging system having a configuration in which an imaging device and a sever device are connected to each other via a communication network is used. The imaging device is a device that performs processing such as photographing an image (a video or a still image), and the server device is a device that performs processing such as storing an image photographed by the imaging device. In the imaging system above, various types of data are transferred between the imaging device and the server device.

As an example of the imaging system including the imaging device and the server device, a system that includes an endoscope system including an endoscope and an endoscopic image recording device and a storing server, and the like are known (see, for example, Japanese Laid-Open Patent Publication No. 2002-34907).

SUMMARY

In one aspect of the present invention, an imaging system including an imaging device connected to a first communication network and a first server device connected to the first communication network is provided that includes a network interface unit configured to transfer data that is formed of video data and data other than the video data, the network interface unit including a first logical port that is used to transfer the video data and a second logical port that is used to transfer the data other than the video data, a measuring unit that measures a data transfer amount of the second logical port included in the network interface unit, and a band control unit that sets a transfer band of the first logical port in such a way that the data other than the video data is transferred on the second logical port, according to the data transfer amount measured by the measuring unit.

In another aspect of the present invention, an imaging device configured to communicate with a server device connected to a communication network is provided, the imaging device including a network interface unit configured to transfer, to the server device, data that is formed of video data and data other than the video data, the network interface unit including a first logical port that is used to transfer the video data and a second logical port that is used to transfer the data other than the video data; a measuring unit that measures a data transfer amount of the second logical port included in the network interface unit; and a band control unit that sets a transfer band of the first logical port in such a way that the data other than the video data is transferred on the second logical port, according to the data transfer amount measured by the measuring unit.

BRIEF DESCRIPTION OF DRAWINGS

FIG. 1 illustrates an exemplary configuration of a medical imaging system according to a first embodiment.

FIG. 3 is a flowchart illustrating an example of processing relating to a transfer band control operation performed by the medical imaging device according to the first embodiment.

FIG. 4 illustrates an exemplary configuration of a medical imaging system according to a second embodiment.

FIG. 6 is a flowchart illustrating an example of processing relating to a transfer band control operation performed by the medical imaging device according to the second embodiment.

FIG. 7 illustrates an exemplary configuration of a medical imaging device according to a variation.

DESCRIPTION OF EMBODIMENTS

Embodiments of the present invention are described below with reference to the drawings.

The embodiments below are described under the assumption that an imaging system according to the present invention is applied to the medical field, and is used as a medical imaging system. However, this is an example, and of course, the imaging system according to the present invention may be applied to another field, and may be used as another type of imaging system.

First Embodiment

FIG. 1 illustrates an exemplary configuration of a medical imaging system according to a first embodiment of the present invention.

As illustrated in FIG. 1, a medical imaging system 100 according to this embodiment includes a medical imaging device 200, a communication network 300, and a server device 400, and the medical imaging system 100 has a configuration in which each of the medical imaging device 200 and the server device 400 is connected to the communication network 300. The medical imaging device 200, the communication network 300, and the server device 400 are examples of an imaging device, a first communication network, and a first server device.

Each of the medical imaging device 200 and the server device 400 includes a logical port A used to transfer video data and a logical port B used to transfer data other than the video data. The logical port A is also a logical port that is used by an application used to transfer video data. The logical port B is also a logical port that is used by an application used to transfer data other than the video data.

The logical port A and the logical port B are examples of a first logical port and a second logical port.

The communication network 300 has a network environment conforming to, for example, 100BASE-TX (an effective throughput is about 40 Mbps (Megabits per second)).

Figure 2:
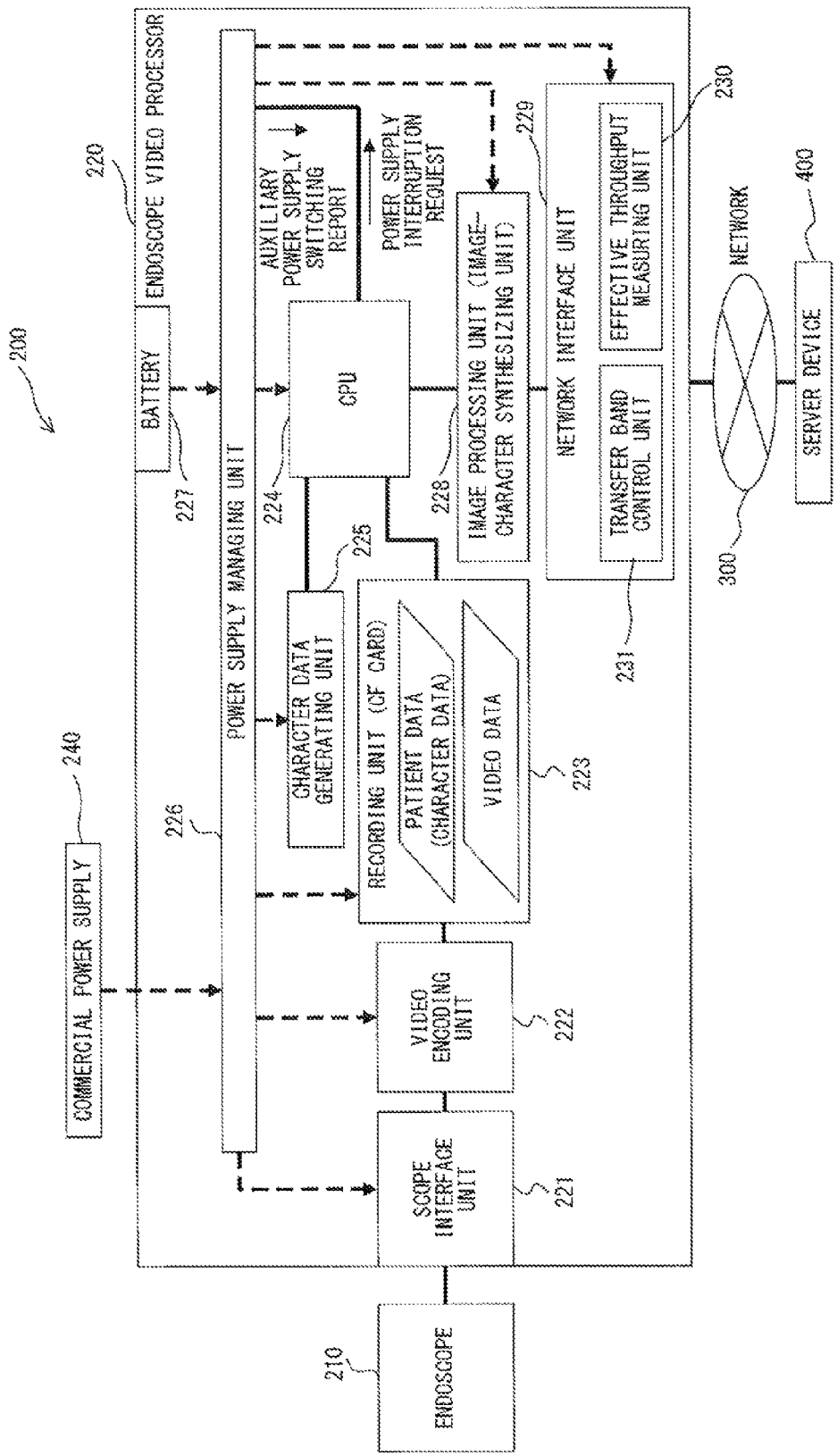
FIG. 2 illustrates an exemplary configuration of a medical imaging device according to the first embodiment.

FIG. 2 illustrates an exemplary configuration of the medical imaging device 200.

As illustrated in FIG. 2, the medical imaging device 200 includes an endoscope 210 and an endoscope video processor 220, and the medical imaging device 200 has a configuration in which the endoscope 210 and the endoscope video processor 220 are connected to each other.

The endoscope 210 outputs, to the endoscope video processor 220, a video signal obtained by capturing a subject image in accordance with an imaging instruction of a user (for example, a doctor). In the description below, it is assumed as an example that the endoscope 210 outputs, to the endoscope video processor 220, a video signal of a video obtained in accordance with a video imaging instruction of a user.

The endoscope video processor 220 includes a scope interface unit 221, a video encoding unit 222, a recording unit 223, a CPU (Central Processing Unit) 224, a character data generating unit 225, a power supply managing unit 226, a battery 227, an image processing unit 228, and a network interface unit 229. The recording unit 223 and the battery 227 are examples of a video data recording unit and an auxiliary power supply.

The scope interface unit 221 converts the video signal output from the endoscope 210 into image data, for example, by performing prescribed signal processing and A/D (Analog-to-Digital) conversion, and the scope interface unit 221 outputs the image data to the video encoding unit 222.

The video encoding unit 222 encodes the image data output from the scope interface unit 221 in a prescribed format (such as Motion JPEG (Motion Joint Photographic Experts Group), MPEG (Moving Picture Experts Group) 1, or MPEG2), and the video encoding unit 222 outputs the encoded image data to the recording unit 223.

Examples of the recording unit 223 include a CF (CompactFlash) card, and the recording unit 223 records the encoded image data (video data) that has been output from the video encoding unit 222. The recording unit 223 also records patient data (an example of personal data) or the like. The patient data is also character data, and the patient data is generated by the character data generating unit 225. Video data and corresponding patient data are recorded in the recording unit 223 in association with each other, as needed.

The CPU 224 reads and executes a program stored in a memory (not illustrated) so as to control the entire operation of the medical imaging device 200.

The character data generating unit 225 generates various types of character data. As an example, the character data generating unit 225 generates patient data on the basis of data relating to a patient that is input via an operating unit (not illustrated), or data relating to a patient that is transmitted from an external device connected to the communication network 300.

The power supply managing unit 226 manages power supply from an external commercial power supply 240 or the battery 227 to respective units in the medical imaging device 200 (for example, the scope interface unit 221, the video encoding unit 222, the recording unit 223, the CPU 224, the character data generating unit 225, the image processing unit 228, the network interface unit 229, and the like) (see dotted-line arrows in FIG. 2).

The image processing unit 228 performs various types of image processing. As an example, the image processing unit 228 performs a process of synthesizing the video data recorded in the recording unit 223 and the associated patient data (character data) during photographing of a video. The video data that has been synthesized with the patient data by the image processing unit 228, as described above, is displayed as a live video on a display unit (not illustrated).

The network interface unit 229 is connected to the communication network 300, and performs data transfer, for example, from/to the server device 400. In addition, the network interface unit 229 includes an effective throughput measuring unit 230 and a transfer band control unit 231. The effective throughput measuring unit 230 and the transfer band control unit 231 are examples of a measuring unit and a band control unit.

The effective throughput measuring unit 230 measures an effective throughput (a data transfer amount) per prescribed time period of the logical port B. In this embodiment, it is assumed that the prescribed time period is one minute, but is not limited to this.

The transfer band control unit 231 controls transfer bands of the logical port A and the logical port B according to the effective throughput measured by the effective throughput measuring unit 230.

Similarly to the medical imaging device 200, the server device 400 includes a CPU, and a network interface unit including an effective throughput measuring unit and a transfer band control unit, although these are not illustrated.

FIG. 3 is a flowchart illustrating an example of processing relating to a transfer band control operation performed by the medical imaging device 200. This processing is performed by the CPU 224 reading and executing a program stored in a memory (not illustrated).

As illustrated in FIG. 3, when the CPU 224 records and stores, in the recording unit 223, video data obtained in accordance with a video imaging instruction of a user (S101), the CPU 224 starts to transfer the video data to the server device 400 (S102). At this point in time, it is assumed that a transfer band of the logical port A used to transfer video data is set to 50 Mbps (this corresponds to 50% of the entirety of a transfer band) and that the remaining transfer band (50 Mbps) is set to be a transfer band of the logical port B used to transfer data other than the video data.

The CPU 224 then determines whether transfer of video data has been completed (S103). When the determination result is No, the effective throughput measuring unit 230 measures an effective throughput per one minute of the data other than the video data, namely, an effective throughput per one minute in the logical port B, under the control of the CPU 224 (S104).

The CPU 224 determines whether the effective throughput per one minute that has been measured in S104 is greater than or equal to 20 Mbps (this corresponds to 50% of an effective throughput of the communication network 300) (S105). When the determination result is Yes, the transfer band control unit 231 sets a transfer band of the logical port A used to transfer video data to 20 Mbps (this corresponds to 20% of the entirety of a transfer band) under the control of the CPU 224 (S106) 20 Mbps is also a value that is estimated to make an effective throughput be about 8 Mbps. Consequently, the remaining transfer band (80 Mbps) is set to be a transfer band of the logical port B used to transfer data other than the video data.

When the determination result in S105 is No, the CPU 224 determines whether the effective throughput per one minute that has been measured in S104 is greater than or equal to 5 Mbps (this corresponds to 12.5% of the effective throughput of the communication network 300) (S107). When the determination result is Yes, the transfer band control unit 231 sets a transfer band of the logical port A used to transfer video data to 50 Mbps (this corresponds to 50% of the entirety of a transfer band) under the control of the CPU 224 (S108) 50 Mbps is also a value that is estimated to make an effective throughput be about 20 Mbps. Consequently, the remaining transfer band (50 Mbps) is set to be a transfer band of the logical port B used to transfer data other than the video data.

When the determination result in S107 is No, the transfer band control unit 231 sets a transfer band of the logical port A used to transfer video data to 70 Mbps (this corresponds to 70% of the entirety of a transfer band) under the control of the CPU 224 (S109) 70 Mbps is also a value that is estimated to make an effective throughput be about 28 Mbps. Consequently, the remaining transfer band (30 Mbps) is set to be a transfer band of the logical port B used to transfer data other than the video data.

Following S106, S108, or S109, processing returns to S103.

When the determination result in S103 is Yes, this processing is finished.

A transfer band control operation performed by the server device 400 is basically similar to the operation performed by the medical imaging device 200, although this is not illustrated. Namely, in the transfer band control operation performed by the server device 400, processing after video data starts to be transferred from the medical imaging device 200 to the server device 400 is similar to the processes of S103 to S109 illustrated in FIG. 3.

As described above, in the medical imaging system 100 according to this embodiment, when an effective throughput per one minute of data other than video data increases during transfer of the video data from the medical imaging device 200 to the server device 400, a transfer band of the video data is set to be narrow, and a transfer band of the data other than the video data is set to be wide. When the effective throughput per one minute of the data other than the video data decreases during transfer of the video data from the medical imaging device 200 to the server device 400, the transfer band of the video data is set to be wide, and the transfer band of the data other than the video data is set to be narrow. Accordingly, in the medical imaging system 100, the data other than the video data can be transferred without delay, and the time needed to transfer the video data can be reduced as much as possible.

In the transfer band control operation performed by the medical imaging device 200 (see FIG. 3), in a case in which power supply from the external commercial power supply 240 is interrupted, for example, because a user turns off a power switch (not illustrated) of the medical imaging device 200 during transfer of video data, the following operation, for example, may be performed in the medical imaging device 200. In this case, the power supply managing unit 226 may control power supply to respective units needed to transfer the video data (for example, the recording unit 223, the CPU 224, the network interface unit 229, and the like) to be performed from the battery 227 such that transfer of the video data is continued, and the power supply managing unit 226 may control power supply from the battery 227 to be interrupted after transfer of the video data has been completed. More specifically, when the power supply managing unit 226 detects interruption of power supply from the external commercial power supply 240 during transfer of video data, the power supply managing unit 226 switches a power supply source from the external commercial power supply 240 to the battery 227, and transmits a report (an auxiliary power supply switching report) to the CPU 224. Upon receipt of the report, the CPU 224 issues a request to interrupt power supply from the battery 227 (a power supply interruption request) to the power supply managing unit 226, after transfer of the video data has been completed. Upon receipt of the request, the power supply managing unit 226 interrupts the power supply from the battery 227 in accordance with the request. When the power supply managing unit 226 detects power supply from the external commercial power supply 240, the power supply managing unit 226 performs control to switch a power supply source from the battery 227 to the external commercial power supply 240 so as to supply power from the external commercial power supply 240 to the respective units in the medical imaging device 200. The operation above allows transfer of video data to be continued without interruption, even when power supply from the external commercial power supply 240 is interrupted during transfer of the video data. The operation above is not limited to transfer of video data, and may be applied to transfer of data other than the video data Second Embodiment FIG. 4 illustrates an exemplary configuration of a medical imaging system according to a second embodiment of the present invention.

As illustrated in FIG. 4, a medical imaging system 500 according to this embodiment includes a medical imaging device 600, a communication network 700, and a server device 800, and the medical imaging system 500 has a configuration in which each of the medical imaging device 600 and the server device 800 is connected to the communication network 700. The medical imaging device 600, the communication network 700, and the server device 800 are examples of an imaging device, a first communication network, and a first server device.

Each of the medical imaging device 600 and the server device 800 includes a logical port A used to transfer video data and a logical port B used to transfer data other than the video data. The logical port A is also a logical port that is used by an application used to transfer video data. The logical port B is also a logical port that is used by an application used to transfer data other than the video data. The logical port A and the logical port B are examples of a first logical port and a second logical port.

Each of the medical imaging device 600 and the server device 800 also includes a physical port A that is used to transfer video data, and a physical port B that is used to transfer data other than the video data, or the video data and the data other than the video data. The physical port A and the physical port B are examples of a first physical port and a second physical port.

The communication network 700 has a network environment in which each of a network environment between the physical port A of the medical imaging device 600 and the physical port A of the server device 800 and a network environment between the physical port B of the medical imaging device 600 and the physical port B of the server device 800 conforms, for example, to 100BASE-TX (an effective throughput is about 40 Mbps). Hereinafter, the network environment between the physical port A of the medical imaging device 600 and the physical port A of the server device 800 is also referred to as infrastructure to transfer a video. The network environment between the physical port B of the medical imaging device 600 and the physical port B of the server device 800 is also referred to as infrastructure to transfer other data.

Figure 5:
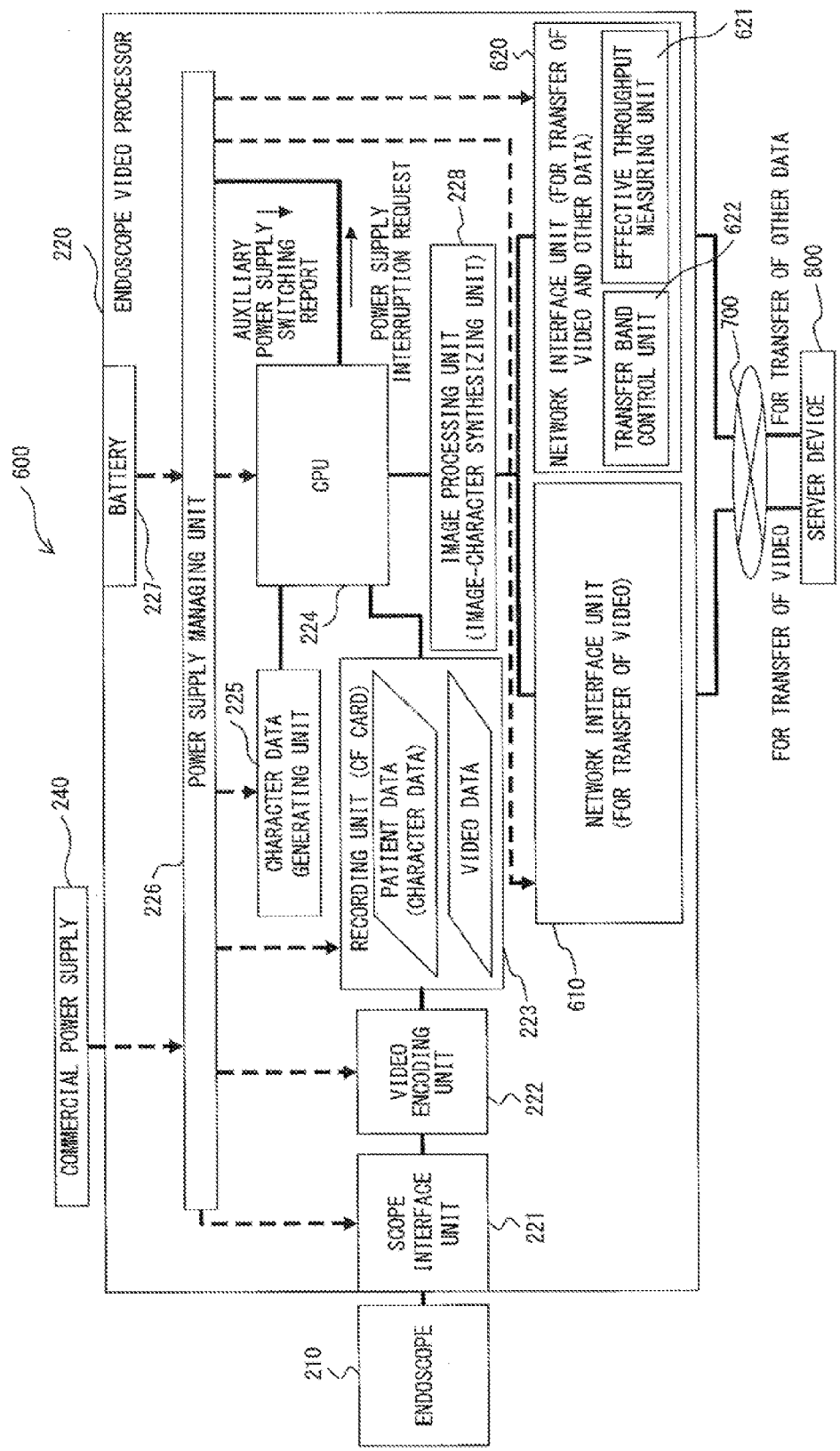
FIG. 5 illustrates an exemplary configuration of a medical imaging device according to the second embodiment.

FIG. 5 illustrates an exemplary configuration of the medical imaging device 600.

As illustrated in FIG. 5, a configuration of the medical imaging device 600 is basically similar to the configuration of the medical imaging device 200 illustrated in FIG. 2, except that the medical imaging device 600 includes two network interface units 610 and 620.

The network interface unit 610 corresponds to the physical port A, and the network interface unit 610 is connected to infrastructure to transfer a video, and transfers video data, for example, from/to the server device 800.

The network interface unit 620 corresponds to the physical port B, and the network interface unit 620 is connected to infrastructure to transfer other data, and transfers data other than video data, or the video data and the data other than the video data, for example, from/to the server device 800. The network interface unit 620 includes an effective throughput measuring unit 621 and a transfer band control unit 622. The effective throughput measuring unit 621 and the transfer band control unit 622 are examples of a measuring unit and a band control unit.

The effective throughput measuring unit 621 measures an effective throughput per prescribed time period of the logical port B in the network interface unit 620 (the physical port B). Also in this embodiment, it is assumed that the prescribed time period is one minute, but is not limited to this.

The transfer band control unit 622 controls transfer bands of the logical port A and the logical port B in the network interface unit 620 (the physical port B) in accordance with the effective throughput measured by the effective throughput measuring unit 621.

The other components are the same as the components illustrated in FIG. 2, and the description thereof is omitted. In the medical imaging device 600 illustrated in FIG. 5, the same components as the components illustrated in FIG. 2 are denoted by the same reference numerals.

Similarly to the medical imaging device 600, the server device 800 includes a CPU, a network interface unit that corresponds to the physical port A, and a network interface unit that corresponds to the physical port B, although these are not illustrated. The network interface unit that corresponds to the physical port B includes an effective throughput measuring unit and a transfer band control unit, similarly to the network interface unit 620.

FIG. 6 is a flowchart illustrating an example of processing relating to a transfer band control operation performed by the medical imaging device 600. This processing is performed by the CPU 224 reading and executing a program stored in a memory (not illustrated).

As illustrated in FIG. 6, when the CPU 224 records and stores, in the recording unit 223, video data obtained in accordance with a video imaging instruction of a user (S201), the CPU 224 starts to transfer the video data to the server device 800 (S202). At this point in time, it is assumed as an example that a transfer band of the logical port A in the physical port B is set to 20 Mbps (this corresponds to 20% of the entirety of a transfer band in the physical port B), and that the remaining transfer band (80 Mbps) in the physical port B is set to be a transfer band of the logical port B in the physical port 13.

The CPU 224 then determines whether transfer of video data has been completed (S203). When the determination result is No, the effective throughput measuring unit 621 measures an effective throughput per one minute of data other than the video data in the network interface unit 620 connected to infrastructure to transfer other data, namely, an effective throughput per one minute of the logical port B in the physical port B, under the control of the CPU 224 (S204).

The CPU 224 determines whether the effective throughput per one minute that has been measured in S204 is greater than or equal to 20 Mbps (this corresponds to 50% of an effective throughput of the infrastructure to transfer other data) (S205). When the determination result is Yes, the transfer band control unit 622 sets a transfer band of video data in the network interface unit 620, namely, a transfer band of the logical port A in the physical port B, to zero, under the control of the CPU 224. Consequently, the remaining transfer band in the physical port B, namely, the entirety of a transfer band (100 Mbps) of the physical port B, is set to be a transfer band of the logical port B in the physical port B. Accordingly, in this case, the infrastructure to transfer other data is not used to transfer a video.

When the determination result in S205 is No, the CPU 224 determines whether the effective throughput per one minute that has been measured in S204 is greater than or equal to 5 Mbps (this corresponds to 12.5% of the effective throughput of the infrastructure to transfer other data) (S207) When the determination result is Yes, the transfer band control unit 622 sets a transfer band of video data in the network interface unit 620, namely, a transfer band of the logical port A in the physical port B, to 20 Mbps (this corresponds to 20% of the entirety of a transfer band in the physical port B) under the control of the CPU 224 (S208) 20 Mbps is also a value that is estimated to make an effective throughput be about 8 Mbps. Consequently, the remaining transfer band (80 Mbps) in the physical port B is set to be a transfer band of the logical port B in the physical port B.

When the determination result in S207 is No, the transfer band control unit 622 sets a transfer band of video data in the network interface unit 620, namely, a transfer band of the logical port A in the physical port B, to 50 Mbps (this corresponds to 50% of the entirety of a transfer band in the physical port B) under the control of the CPU 224 (S209) 50 Mbps is also a value that is estimated to make an effective throughput be about 20 Mbps. Consequently, the remaining transfer band (50 Mbps) in the physical port B is set to be a transfer band of the logical port B in the physical port B.

Following S206, S208, or S209, processing returns to S203.

When the determination result in S203 is Yes, and when a value that has been set to be the transfer band of the video data in the network interface unit 620, namely, the transfer band of the logical port A in the physical port B, is not zero at this point in time, the value is set to zero (S210). Consequently, the remaining transfer band in the physical port B, namely, the entirety of a transfer band (100 Mbps) of the physical port B, is set to be a transfer band of the logical port B in the physical port B. Accordingly, in this case, in the infrastructure to transfer other data, a band used to transfer a video is released.

Following S210, this processing is finished.

A transfer band control operation performed by the server device 800 is basically similar to the operation performed by the medical imaging device 600, although this is not illustrated. Namely, in the transfer band control operation performed by the server device 800, processing after video data starts to be transferred from the medical imaging device 600 to the server device 800 is similar to the processes of S203 to S210 illustrated in FIG. 6.

As described above, in the medical imaging system 500 according to this embodiment, video data is transferred from the medical imaging device 600 to the server device 800 by using infrastructure to transfer a video, or the infrastructure to transfer a video and infrastructure to transfer other data. During transfer of the video data, when an effective throughput per one minute of the data other than the video data increases in the network interface unit 620 connected to the infrastructure to transfer other data, a transfer band of the video data is set to be narrow, and a transfer band of the data other than the video data is set to be wide. During transfer of the video data, when an effective throughput per one minute of the data other than the video data decreases in the network interface unit 620, the transfer band of the video data is set to be wide, and the transfer band of the data other than the video data is set to be narrow. Accordingly, in the medical imaging system 500, the data other than the video data can be transferred without delay, and the time needed to transfer the video data can be reduced as much as possible.

In the transfer band control operation performed by the medical imaging device 600 (see FIG. 6), when power supply from the external commercial power supply 240 is interrupted, for example, because a user turns off a power switch (not illustrated) of the medical imaging device 600 during transfer of video data, the following operation, for example, may be performed by the medical imaging device 600, similarly to in the first embodiment. In this case, the power supply managing unit 226 may control power supply to respective units needed to transfer the video data (for example, the recording unit 223, the CPU 224, the network interface units 610 and 620, and the like) to performed from the battery 227 such that the video data continued to be transferred, and the power supply managing unit 226 may control power supply from the battery 227 to be interrupted after transfer of the video data has been completed. The operation above allows the transfer of the video data to be continued without interruption, even when power supply from the external commercial power supply 240 is interrupted during the transfer of the video data. The operation above is not limited to the transfer of the video data, and may be applied to transfer of data other than the video data.

The first and second embodiments have been described above, but various variations to the respective embodiments can be made.

As an example, in the medical imaging device 200 according to the first embodiment or the medical imaging device 600 according to the second embodiment, when power supply from the external commercial power supply 240 is interrupted during transfer of data (for example, video data), power supply to respective units needed to transfer the data may be controlled to be performed from a network device connected to the communication network 300 or 700 such that the data continues to be transferred, and power supply from the network device may be controlled to be interrupted after transfer of the data has been completed. In this case, as an example, the battery 227 is removed from the medical imaging device 200 illustrated in FIG. 2, and the medical imaging device 200 illustrated in FIG. 2 is connected to a PoE (Power over Ethernet) compatible switching hub 301 that is a network device connected to the communication network 300, as illustrated in FIG. 7. When power supply from the external commercial power supply 240 is interrupted during transfer of the data, the power supply managing unit 226 controls power supply to respective units needed to transfer video data to be performed from the switching hub 301 such that transfer of the data is continued, and the power supply managing unit 226 controls power supply from the switching hub 301 to be interrupted after transfer of the video data has been completed. In the variation above, it can be unnecessary to mount the battery 227 onto the medical imaging device 200 or 600.

Figure 8:
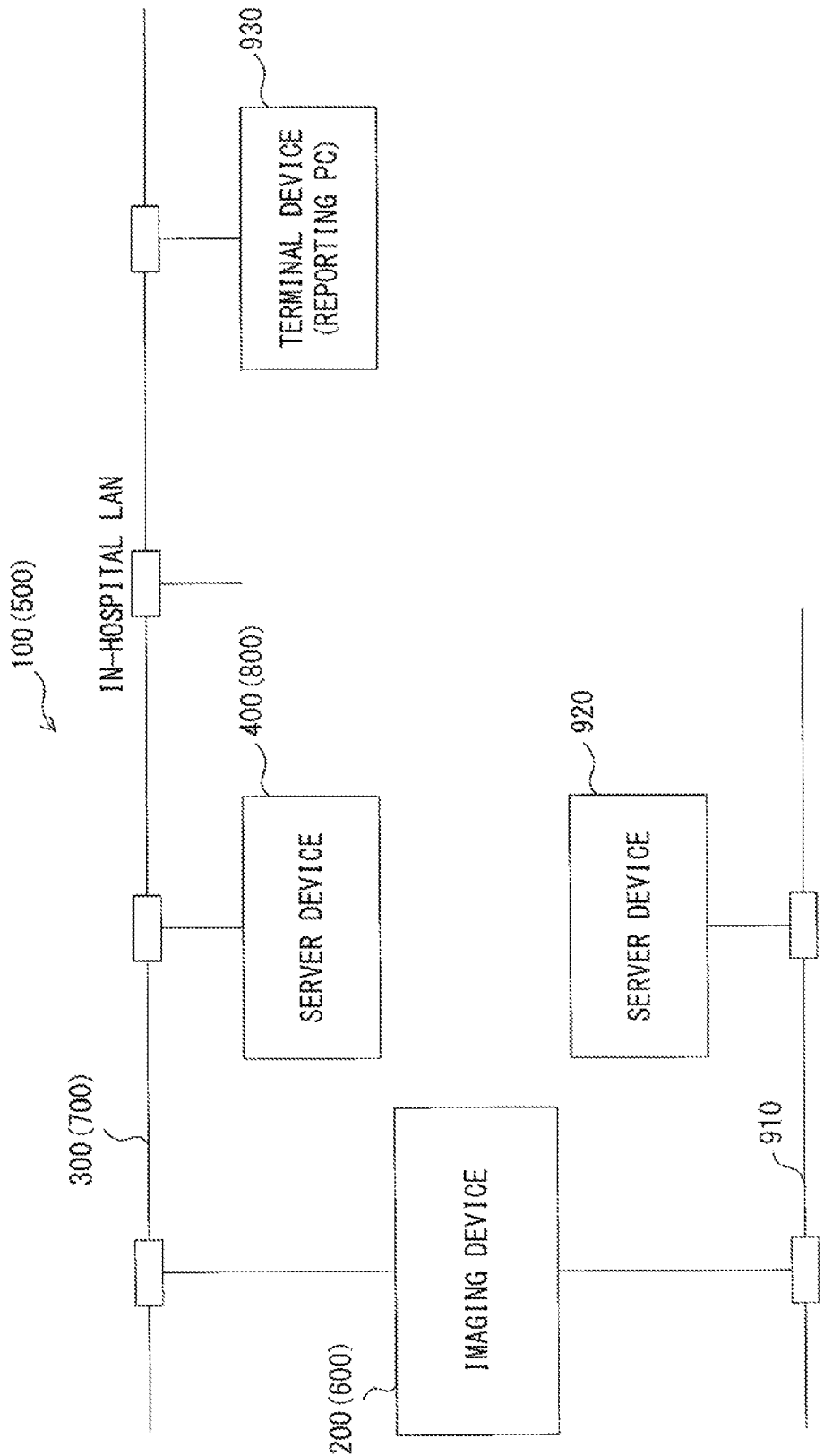
FIG. 8 is a first diagram illustrating an exemplary configuration of a medical imaging system according to a variation.

As another example, the medical imaging system 100 according to the first embodiment or the medical imaging system 500 according to the second embodiment may have a configuration in which the medical imaging device 200 or 600 is further connected to a communication network 910 that is not connected to the communication network 300 or 700 illustrated as an in-hospital LAN and a server device 920 is connected to the communication network 910, as illustrated in FIG. 8. In FIG. 8, connection between the medical imaging device 600 and the communication network 700 and connection between the server device 800 and the communication network 700 are illustrated as one communication line for convenience of explanation (the same applies to FIG. 9 described later). The communication network 910 and the server device 920 are examples of a second communication network and a second sever device. Data (for example, video data) that is transferred from the medical imaging device 200 or 600 via an in-hospital LAN 300 or 700 to the server device 400 or 800 and that is recorded in the server device 400 or 800 may be transferred from the medical imaging device 200 or 600 via the communication network 910 to the server device 920, and may be recorded as original data in the server device 920, The data that is transferred from the medical imaging device 200 or 600 to the server device 400 or 800 and that is recorded in the server device 400 or 800 is then obtained, for example, by a terminal device (such as a reporting PC (Personal Computer)) 930 that is connected to the in-hospital LAN 300 or 700, and is used for reporting. In the variation above, data that is recorded as original data in the server device 920 that is connected to the communication network 910 disconnected from the in-hospital LAN 300 or 700 can reduce a risk of data falsification due to a security threat.

Figure 9:
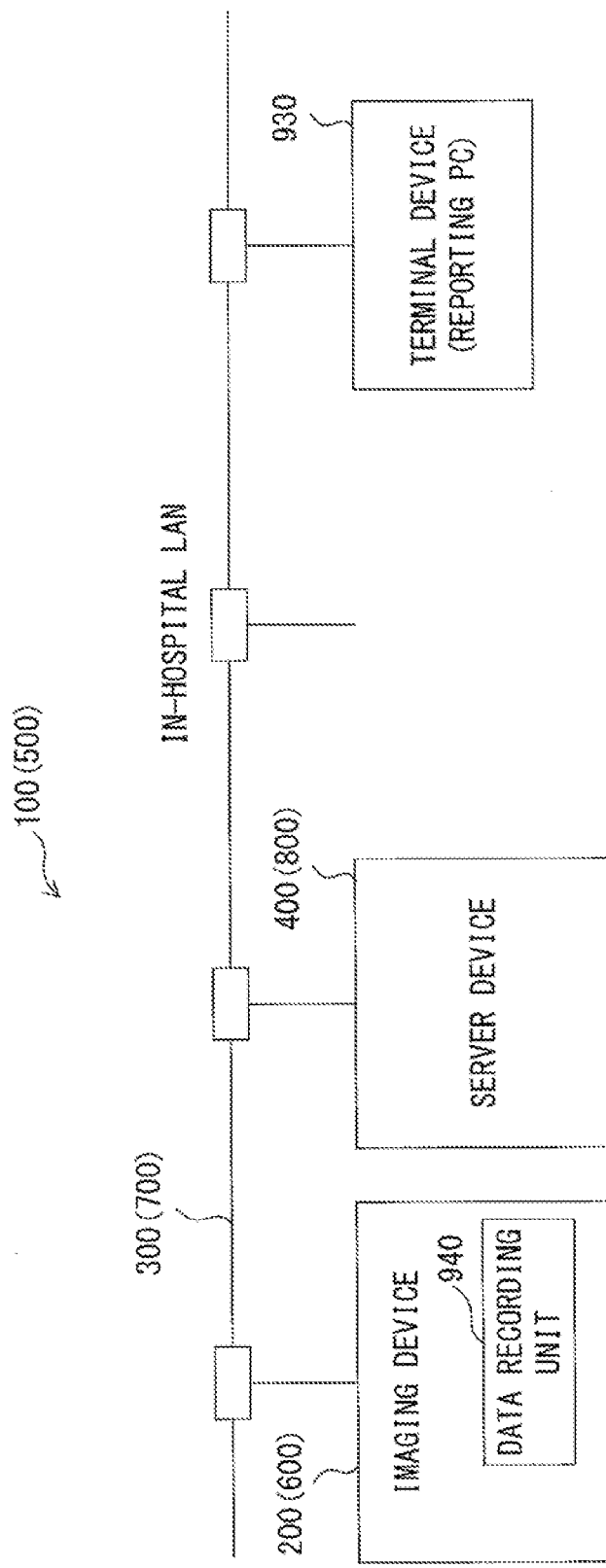
FIG. 9 is a second diagram illustrating an exemplary configuration of a medical imaging system according to a variation.

As another example, the medical imaging system 100 according to the first embodiment or the medical imaging system 500 according to the second embodiment may have a configuration in which the medical imaging device 200 or 600 further includes a data recording unit 940, as illustrated in FIG. 9. Data (for example, video data) that is transferred from the medical imaging device 200 or 600 via the communication network 300 or 700 that is illustrated as an in-hospital LAN to the server device 400 or 800 and that is recorded in the server device 400 or 800 may be also recorded temporarily as original data in the data recording unit 940. The data recording unit 940 may be provided separately from the recording unit 223, or a portion of the recording unit 223 may be shared as the data recording unit 940. The data that is transferred from the medical imaging device 200 or 600 to the server device 400 or 800 and that is recorded in the server device 400 or 800 is then obtained, for example, by the terminal device (for example, the reporting PC (Personal Computer)) 930 that is connected to an in-hospital LAN 300 or 700, and is used for reporting, similarly to in the variation above. In this variation, data recorded as original data in the data recording unit 940 can reduce a risk of data falsification due to security threat.

In the variations described using FIGS. 8 and 9, as an example, when the medical imaging device 200 or 600 transfers data (for example, video data) to the server device 400 or 800, the medical imaging device 200 or 600 may also transfer examination date data relating to the data to the server device 400 or 800. The server device 400 or 800 may detect whether there is a possibility of data falsification on the basis of a date at which the data transferred from the medical imaging device 200 or 600 is recorded and an examination date in the examination date data relating to the data transferred from the medical imaging device 200 or 600. As an example, when there is a difference that is greater than or equal to a specified time period between both of the dates, a report indicating that there is a possibility of data falsification may be issued to an administrator or the like. In this variation, the server device 400 or 800 can detect whether there is a possibility of falsification of the recorded data.

Figure 10:
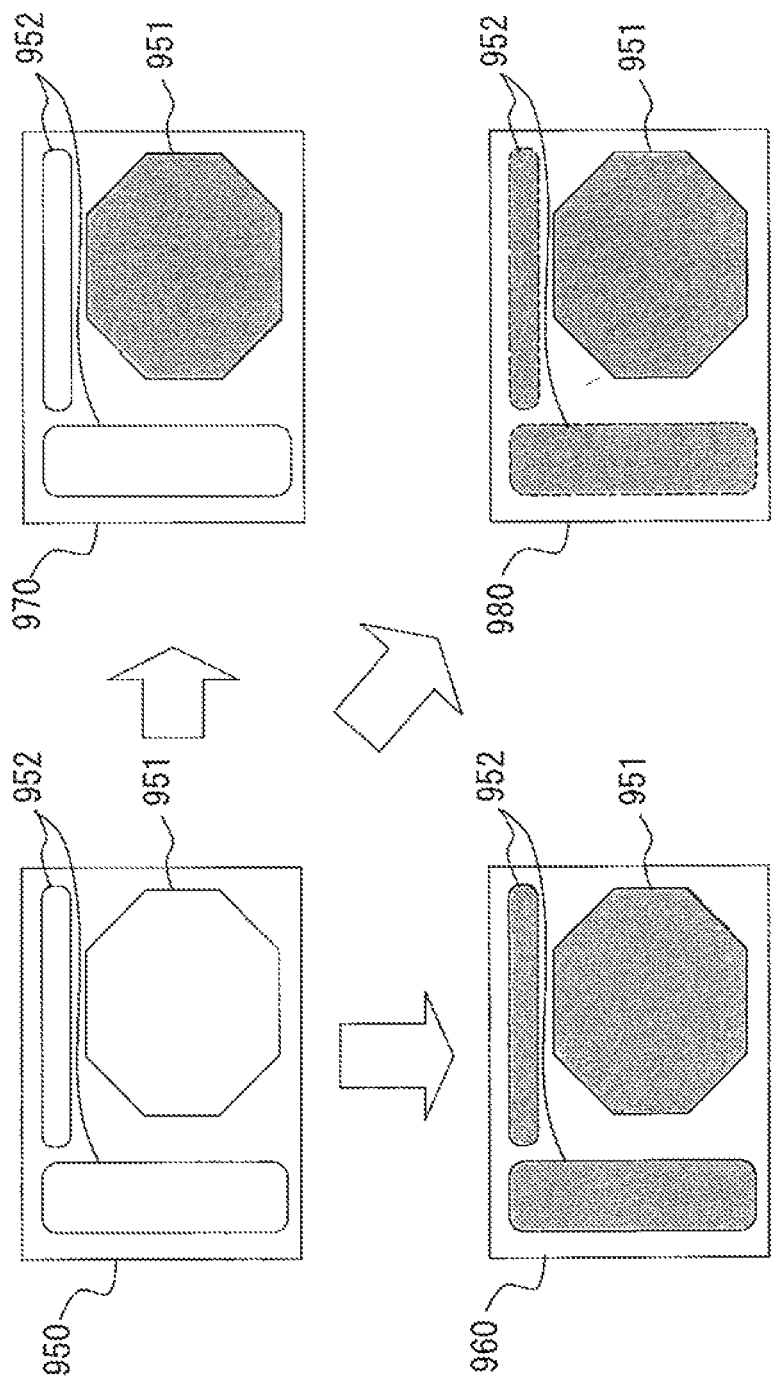
FIG. 10 illustrates an example of a reproduction display according to a variation.

As another example, in the medical imaging system 100 according to the first embodiment, the medical imaging system 500 according to the second embodiment, or a medical imaging system according to the variation illustrated in FIG. 8 or 9, the medical imaging device 200 or 600 may reproduce and display only video data recorded in the recording unit 223, or the video data recorded in the recording unit 223 and patient data associated with the video data on a display unit (not illustrated) in accordance with an instruction of a user (for example, a doctor). The server device 400 or 800 in which video data transferred from the medical imaging device 200 or 600 and patient data associated with the video data are recorded may reproduce and display only the video data, or the video data and the patient data associated to the video data on a display unit (not illustrated) in accordance with a user's instruction. The terminal device 930 illustrated in FIG. 8 or 9 may reproduce and display, on a display unit (not illustrated), only the video data recorded in the server device 400 or 800, or the video data recorded in the server device 400 or 800 and the patient data associated with the video data in accordance with a user's instruction. In this case, a reproduction display is performed as illustrated in FIG. 10, for example. First, a user selects only a video display area 951, or the video display area 951 and a patient information display area 952 on an initial screen 950 of the reproduction display via an operating unit (not illustrated). When the user selects the video display area 951 and the patient information display area 952, a video relating to the video data is reproduced and displayed in the video display area 951, and patient information relating to the patient data is reproduced and displayed in the patient information display area 952, as illustrated on a reproduction display screen 960. In FIG. 10, an area in which a reproduction display is performed is illustrated in grey for convenience of explanation. When a user selects only the video display area 951 on the initial screen 950, a video relating to the video data is reproduced and displayed in the video display area 951, but nothing is displayed in the patient information display area 952, as illustrated on a reproduction display screen 970. In this case, as an example, patient information that is reproduced and displayed in the patient information display area 952 and a background of the patient information display area 952 may be colored in the same color, as illustrated in a reproduction display screen 980 such that the patient information is not displayed consequently. On the reproduction display screen 980 in FIG. 10, the patient information display area 952 in which the reproduced and displayed patient information and the background are colored in the same color is illustrated with a dotted line, for convenience of explanation. In this variation, a user can select whether the user displays only video data, or the video data and patient data associated with the video data, in accordance with the situation.

The embodiments described above give specific examples of the present invention in order to easily understand the invention, and the present invention is not limited to the embodiments described above. Various variations or modifications of the present invention can be made without departing from the spirit of the present invention specified in the claims.

As described above, according to the present invention, data other than video data can be transferred without delay, and the time needed to transfer the video data can be reduced as much as possible.

What is claimed is:

1. An imaging system including at least one imaging device connected to a first communication network, and a first server device connected to the first communication network, the imaging system comprising: a network interface unit configured to transfer data that is formed of video data and data other than the video data, the network interface unit including a first logical port that is used to transfer the video data and a second logical port that is used to transfer the data other than the video data; a measuring unit that measures a data transfer amount of the second logical port included in the network interface unit; and a band control unit that sets a transfer band of the first logical port in such a way that the data other than the video data is transferred on the second logical port, according to the data transfer amount measured by the measuring unit.

2. The imaging system according to claim 1, wherein the band control unit sets the transfer band of the first logical port according to the data transfer amount measured by the measuring unit, and sets the transfer band of the second logical port by allocating, to the second logical port, the transfer band obtained by subtracting the transfer band of the first logical port from an entirety of a transfer band of the network interface unit.

3. The imaging system according to claim 1, wherein when the data transfer amount measured by the measuring unit is greater than or equal to a first threshold, the band control unit sets the transfer band of the first logical port in such a way that the transfer band of the second logical port is wider than the transfer band of the first logical port.

4. The imaging system according to claim 3, wherein when the data transfer amount is less than or equal to a second threshold that is less than the first threshold, the band control unit sets the transfer band of the first logical port in such a way that the transfer band of the second logical port is narrower than the transfer band of the first logical port.

5. The imaging system according to claim 4, wherein when the data transfer amount is less than the first threshold, and is greater than the second threshold, the band control unit sets the transfer band of the first logical port in such a way that the transfer band of the second logical port is equal to the transfer band of the first logical port.

6. The imaging system according to claim 1, wherein each of the imaging device and the first server device includes the network interface unit, the network interface unit included in each of the imaging device and the first server device includes: a first physical port to transfer the video data, and a second physical port to transfer the data other than the video data, or the video data and the data other than the video data, the measuring unit measures the data transfer amount of the second logical port in the second physical port, and the band control unit sets the transfer band of the first logical port in the second physical port in such a way that the data other than the video data is transferred on the second logical port in the second physical port, according to the data transfer amount measured by the measuring unit.

7. The imaging system according to claim 1, further comprising: a second server device that is connected to a second communication network that is not connected to the first communication network, wherein the at least one imaging device is also connected to the second communication network, and data that is transferred from the at least one imaging device via the first communication network to the first server device and that is recorded in the first server device is also transferred from the at least one imaging device via the second communication network to the second server device, and is also recorded in the second server device.

8. The imaging system according to claim 1, the at least one imaging device further comprising a data recording unit, wherein the data that is transferred from the at least one imaging device via the first communication network to the first server device and that is recorded in the first server device is also recorded in the data recording unit.

9. The imaging system according to claim 7, wherein when transferring the data to the first server device, the at least one imaging device also transfers date data relating to the data to the first server device, and the first server device detects whether there is a possibility of falsification of the data on the basis of date at which the data transferred from the at least one imaging device is recorded and the date data relating to the data transferred from the at least one imaging device.

10. The imaging system according to claim 1, the at least one imaging device further comprising: an auxiliary power supply; and a power supply managing unit that manages power supply to respective units of the at least one imaging device, wherein in the at least one imaging device, when power supply from a commercial power supply is interrupted during transfer of data, the power supply managing unit controls power supply to respective units needed to transfer the data to be performed from the auxiliary power supply such that the transfer of the data is continued, and controls power supply from the auxiliary power supply to be interrupted after the transfer of the data is completed.

11. The imaging system according to claim 1, the at least one imaging device further comprising: a power supply managing unit that manages power supply to respective units of the at least one imaging device, wherein in the at least one imaging device, when power supply from a commercial power supply is interrupted during transfer of data, the power supply managing unit controls power supply to respective units needed to transfer the data to be performed from a network device connected to the first communication network such that the transfer of the data is continued, and controls power supply from the network device to be interrupted after the transfer of the data is completed.

12. The imaging system according to claim 1, the at least one imaging device further comprising: a video data recording unit that records the video data and personal data in association with each other, wherein each of the at least one imaging device and the first server device that records the video data transferred from the at least one imaging device and the personal data associated with the video data displays only the video data, or the video data and the personal data associated with the video data.

13. An imaging device configured to communicate with a server device connected to a communication network, the imaging device comprising: a network interface unit configured to transfer, to the server device, data that is formed of video data and data other than the video data, the network interface unit including a first logical port that is used to transfer the video data and a second logical port that is used to transfer the data other than the video data; a measuring unit that measures a data transfer amount of the second logical port included in the network interface unit; and a band control unit that sets a transfer band of the first logical port in such a way that the data other than the video data is transferred on the second logical port, according to the data transfer amount measured by the measuring unit.

\* \* \* \* \*